United States Patent [19]
Zell

[11] 4,429,685
[45] Feb. 7, 1984

[54] SURGICAL PROCEDURE

[76] Inventor: Timothy G. Zell, Box 982, Ukiah, Calif. 95482

[21] Appl. No.: 398,208

[22] Filed: Jul. 14, 1982

Related U.S. Application Data

[63] Continuation of Ser. No. 175,029, Aug. 4, 1980, abandoned.

[51] Int. Cl.³ .............................................. A61K 31/505
[52] U.S. Cl. ................................................. 128/1 R
[58] Field of Search ........................................ 128/1 R

[56] References Cited
PUBLICATIONS

W. Franklin Dove, Physiology of Horn Growth, *J. of Ex. Zoology*, v. 69, No. 3.
W. Franklin Dove, Artif. Production of the Fabulous Unicorn, *Scientific Monthly*, v. 42, pp. 431–466.
*The Living Unicorn*, by The Living Unicorn, Inc., ©1980 (booklet).

*Primary Examiner*—George F. Lesmes
*Assistant Examiner*—Nancy A. B. Swisher
*Attorney, Agent, or Firm*—Gerald L. Moore

[57] ABSTRACT

This invention relates to a method of growing unicorns in a manner that enhances the overall development of the animal.

5 Claims, 16 Drawing Figures

SURGICAL PROCEDURE

This is a continuation of application Ser. No. 175,029, filed Aug. 4, 1980, now abandoned.

BACKGROUND OF THE INVENTION

The unicorn, both in mythology and history, possesses a unique reputation as being a fearless, courageous and beautiful animal and protector of other beasts. One theory explains the origination of the unicorn as being developed by herds-keepers for protecting the herd. The single center position horn is a lethal weapon for warding off predatory animals. It is thought that the herdsmen did not wish to employ dogs or other animals as guards since they are meat eaters and expensive to keep.

Other theories attribute various magical powers to the horn of the unicorn. In any event the unicorn appears in many early drawings and then seems to have ceased to exist to the extent that for many centuries it was hard to distinguish whether or not the unicorn had actually existed or whether it was a product of man's imagination.

In January 1935 Dr. W. Franklin Dove, a biologist at the University of Maine, wrote for the Journal of Experimental Zoology, in Volume 69, Number 3, an article entitled: The Physiology of Horn Growth, in which he traced various previous efforts at developing a unicorn and documented his own efforts along those lines. Also in the Scientific Monthly dated May 1936, Volume 42; Pages 431-436, Dr. Dove wrote an article entitled: Artificial Production of the Fabulous Unicorn, in which he traced various efforts to grow unicorns. Generally speaking it is reported that all unicorns have been developed by a surgical procedure in which the horn buds of a newly-born animal are transplanted from the usual location to a central position on the front of the animal's skull. It is not generally known that during the first week of development, the horn buds are attached to the skin only and attachment to the skull begins after this period. In other words, horns are the result of separate ossifications that subsequently fuse to the frontal bones of the head rather than being outgrowths of these frontal bones or of the skull. These horn buds initially are supplied with blood through capillaries and only in subsequent stages of development does the horn develop a complex blood circulating system. Such past work has involved the transplanting of the horn buds to a position on the front of the skull or the shifting of the position of pedicled flaps containing the horn bud. Usually the procedure has been performed only upon the family Bovinae to include the five subfamilies Bovinae, Cephalophinae, Hippotraginae, Antilopinae and Caprinae, i.e. cattle, antelopes, sheep and goats.

It is the purpose of the present invention to provide an improved method of forming a unicorned animal having what is thought to be a higher mental capacity and greater physical capabilities.

SUMMARY OF THE INVENTION

The method of forming a unicorn from an animal normally having a horn growing from each side of the head involving the pedicling of first flaps of skin, one on each side of the head and selected to include the horn bud at a time prior to the attachment of the bud to the skull. Second flaps of skin, one to each side of the front of the head and in alignment with the general area of the pineal gland within the skull are also pedicled. The first flaps of skin are lifted away from the skull by pivoting the flaps about the attached end and the second flaps are each moved into the position vacated by the adjacent first flap of skin. The moving of the first flaps of skin into the position vacated by the second flaps of skin positions the horn buds adjacent one another over the pineal gland at the front of the skull. Thereafter the resulting horns grow as one and connect with the frontal portion of the skull directly over the pineal gland to render a unicorn of higher intelligence and physical attributes.

DESCRIPTION OF THE INVENTION

Figure 1A:
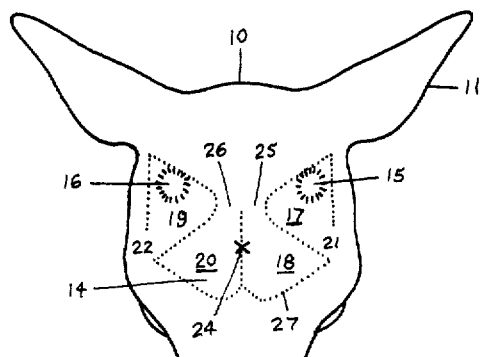
FIGS. 1A through 1D show a first method for moving the two horn buds to an abutting position on the skull of an animal by interchanging pedicled flaps of skin.
Figure 2A:
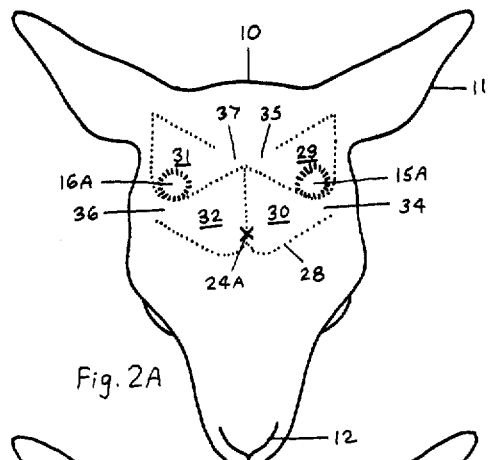
FIGS. 2A through 2D show a second embodiment of the invention.
Figure 1B:
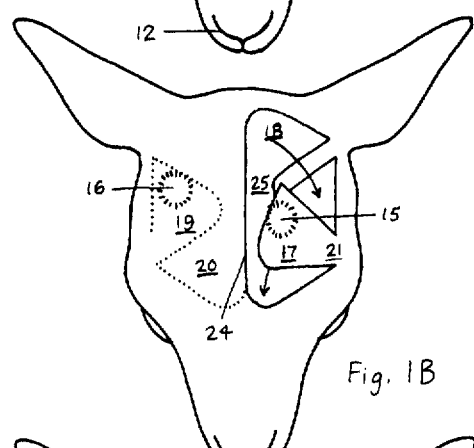
Figure 2B:
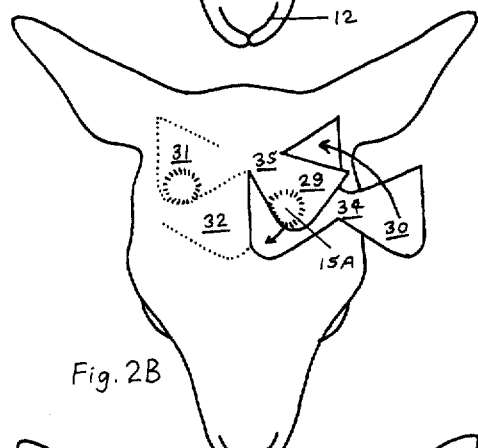

In FIGS. 1A through 1D is shown a first embodiment of the invention comprising a procedure illustrated on the head of a goat 10 showing the ears 11, the nose region 12 and the frontal skull area 14. This head represents that of an animal less than one-week old in that horn buds 15 and 16 are illustrated in the original positions at the upper corners of the front area of the skull. At this age the horn buds are not attached to the head bone but instead are supported by the skin only with no direct attachment with the skull. In normal horn growth connective tissue to the bone adjacent the horn bud starts development after the animal is approximately one-week old and thereafter the resulting horn spike appears to grow out of the skull when in fact it grows independently but does become rigidly attached to the skull. With the initiation of subsequent growth the horn forms a blood supply system, however the horn bud initially is supplied with blood through small capillaries in the skin.

With the horns growing in the ordinary position as shown in FIG. 1A it is thought that there results some restriction in the expansion of the cranial area of the skull in which the brain of the animal is positioned. It is further theorized that such restriction in the growth of the skull can have some effect on the ultimate intelligence of the animal if in fact overall growth of the brain is restricted. It is further reported that unicorns as have been known in the past with the single horn projecting from some area of the frontal portion of the skull have developed into much better guard animals in that the horn in being so positioned is a much more lethal weapon primarily because of the way an animal attacks its enemies with a forward thrust of the head and body. With the horns projecting out the side of the skull, the animal must assume a turned posture or swing its head in order to use the horns and such action diminishes the effectiveness of the attack. Possibly because of the more lethal potential of unicorns, such animals have ceased to be developed over the past several centuries except on an extremely abbreviated and experimental basis.

Figure 1C:
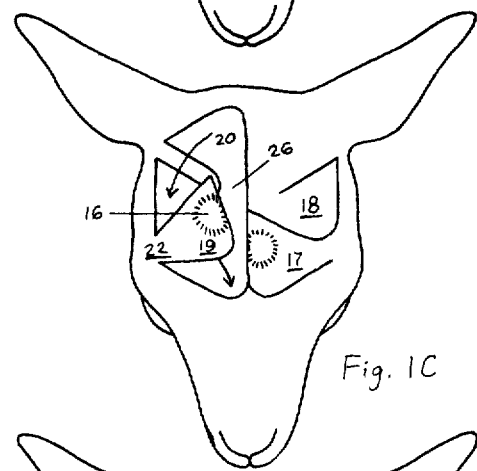
Figure 2C:
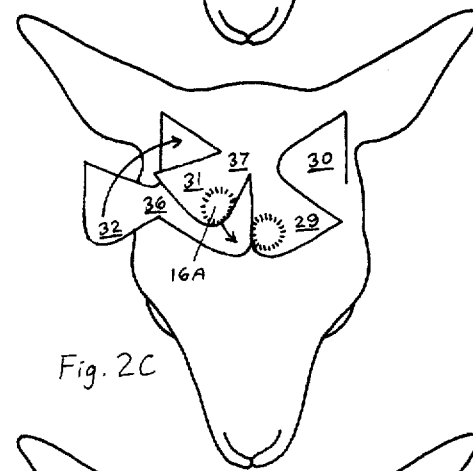
Figure 1D:
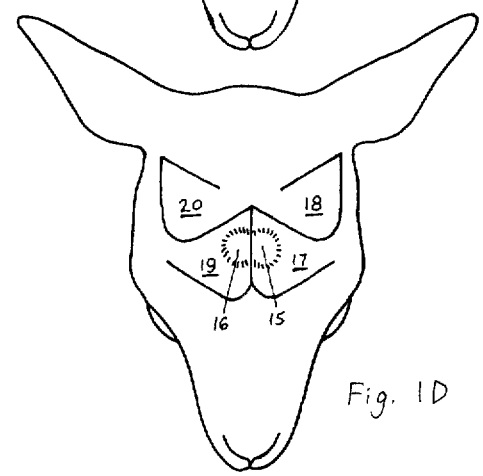
Figure 2D:
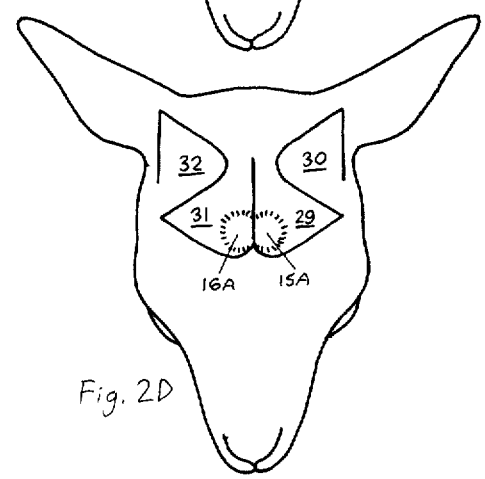

In accordance with the present invention there is taught a method of transposing the horn buds so that the animal will grow as a unicorn with the location of the horn being selected to provide a better-developed and more intelligent animal. As shown in FIGS. 1A through 1D, two flaps 17 and 18 are formed for transposing the horn bud 15 while flaps 19 and 20 are formed for transposing the horn bud 16. For this purpose the skin is cut to form the pedicled flaps such that the connecting areas 21 and 22 of the flaps 17 and 19 are positioned remote from the area 24 at which the horn buds are to be positioned. Additionally the areas 25 and 26 of the flaps 18 and 20 are positioned remote from the original horn bud area and the transposed position. Thus the dotted line 27 illustrates the location of the incisions in this first embodiment method to form the pairs of pedicled flaps with the one flap of each pair including a horn bud. After such incisions are made the flap 18 is lifted in the manner shown in FIG. 1B so as to extend away from the skull while still being connected to the skin by the connecting area 25. Thereafter the flap 17 is pivoted about the area 21 so as to move the horn bud 15 to the transposed area 24. Subsequently as shown in FIG. 1C, the flap 18 is placed back against the skull in the area vacated by the flap 17. Sutures reconnect the adjacent severed areas of the skin.

In the same manner the flaps 19 and 20 are transposed on the left front side of the head to move the horn bud 16 in the manner shown in 1C down to the transposed area. Sutures are made to connect adjacent skin areas together and also to complete the horn bud transposition, the adjacent areas of the flaps 17 and 19 are sutured. Thus in the manner shown the horn buds are transposed into abutting relationship at the transpositioned area 24. Because the flaps are pedicled, the blood supply to the horn bud and skin is never interrupted.

The transposition area at which the horn is to grow is selected with great care. This area 24 is directly over the pineal gland which is within the cranial area of the skull and serves as the master gland of the animal. Beneath this pineal gland is the pituitary gland which is controlled by the pineal gland. Tests have indicated that transposition of the horns of the animal to form a unicorn with the single horn being positioned over the pineal gland has rendered a more intelligent and controllable animal. While not proven, it is thought that the removal of the horns from the upper cranial area permits a better development of the cranial area and the brain of the animal while the single horn over the pineal gland also causes a better development of that gland. The exact reason for this occurrence is not known to the inventor.

In FIG. 2 is shown a second embodiment of the invention performed on an animal head as in the first embodiment. The horn buds 15A and 16A are shown in the ordinary positions in FIG. 2A. Thereafter incisions are made along the dotted lines 28 to form the pedicled flaps 29 and 30 on the right side and 31 and 32 on the left side. Thereafter as shown in FIG. 2B the pedicled flap 30 is raised by pivoting it about the connecting tissue 34 and the flap 29 is pivoted downward about the connecting tissue 35. Thereafter as shown in FIG. 2C the left side flap 32 is lifted by pivoting about the connecting tissue 36 and the flap 31 is pivoted downward about the connecting area 37. Suturing is then achieved along the dark lines of FIG. 2D and the horn buds are positioned in abutting relationship over the transposed area 24A shown in FIG. 2A. As discussed previously, this area for the growth of the single horn is carefully selected.

Figure 3A:
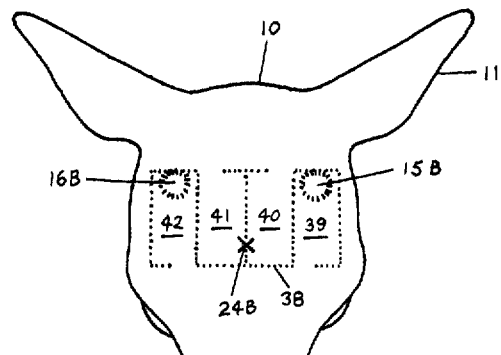
FIGS. 3A through 3D show a third embodiment of the invention.
Figure 3B:
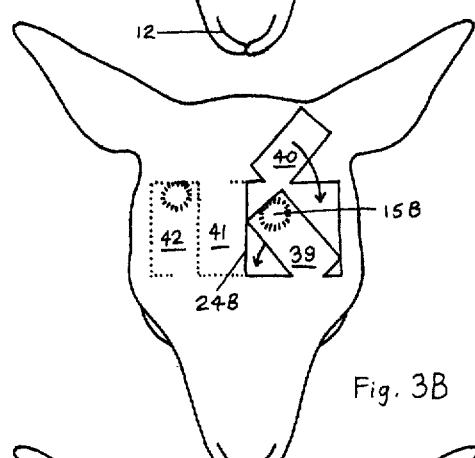

Shown in FIGS. 3A through 3D is yet another embodiment of the invention wherein the head 10 having ears 11 and nose 12 also includes the horn buds 15B and 16B shown in FIG. 3A to be in their normal position. It is desired to transform these horn buds to the area 24B as in the previous embodiment. For this purpose sutures are made along the dotted lines 38 shown in FIG. 3A to form pedicled flaps 39 and 40 at the left frontal area of the head and 41 and 42 on the right frontal area of the head. Thereafter as shown in FIG. 3B the pedicled flap 40 is lifted and the pedicled flap 39 is pivoted counterclockwise to shift the horn bud 15B over the area 24B illustrated in FIG. 3A. Thereafter the pedicled flap 40 is pivoted clockwise to lie parallel to the flap 39 in position to be sutured.

Figure 3C:
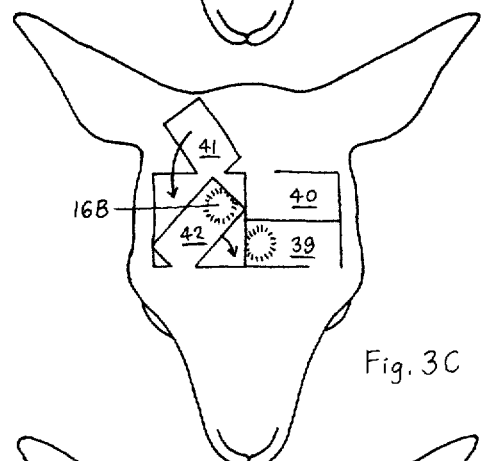
Figure 3D:
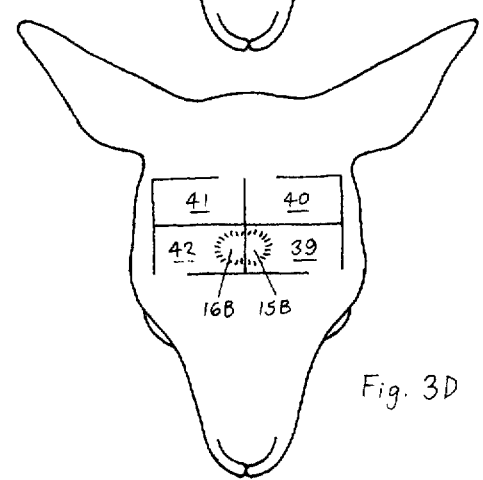

Similarly the pedicled flap 41 is lifted as shown in FIG. 3C and the flap 42 is pivoted clockwise to bring the horn bud in close proximity to the horn bud 15 in the area 24B. Flap 41 is then pivoted in the counterclockwise direction to a position adjacent to flap 42 and suturing is accomplished with the completed transposition of the horn buds appearing as shown in FIG. 3D.

Figure 4A:
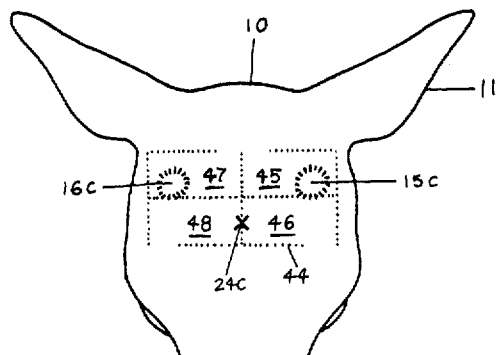
FIGS. 4A through 4D show a fourth embodiment of the invention.
Figure 4B:
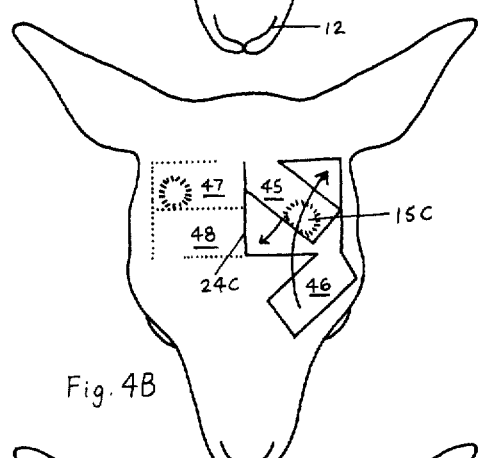

FIG. 4A shows another embodiment of the invention in which the horn buds 15C and 16C are desired to be transposed to the area 24C. For this purpose incisions are made along the dotted lines 44 to form the pedicled flaps 45 and 46 on the right frontal area and 47 and 48 on the left frontal area of the head. The flap 44 is then lifted in the manner shown in FIG. 4B and the flap 45 is pivoted in a clockwise direction to bring the horn bud 15C into close proximity to the area 24C. Thereafter the flap 46 is pivoted in the clockwise direction to lie parallel to the flap 45 and is sutured in position.

Figure 4C:
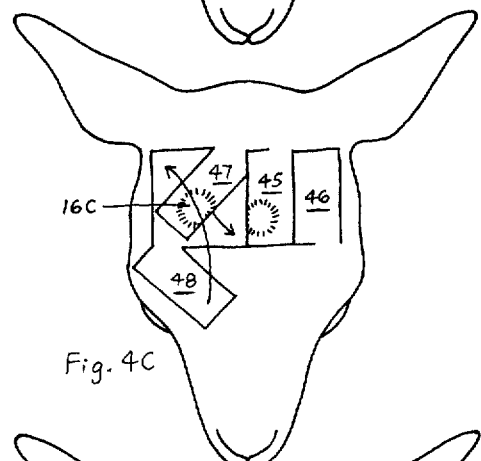
Figure 4D:
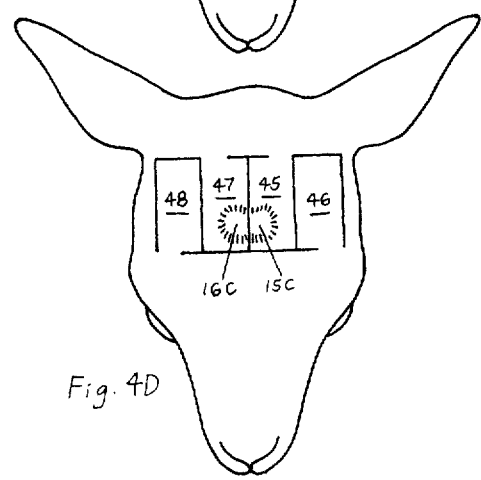

In the manner shown in FIG. 4C the left frontal area of the head is transformed by pivoting the pedicled flap 48 outward away from the skull and moving the flap 47 in the counter-clockwise direction to shift the horn bud 16C into the area 24C. The flap 48 is then pivoted in the counterclockwise direction and positioned adjacent the flap 47 for suturing. The completed transposition appears as shown in FIG. 4D.

Thus it has been shown that by making incisions to include the horn bud on the left and right sides of the frontal area of the animal's head with the connecting tissue only positioned remote to the original position and the transformed position of the horn bud and by forming another pedicled flap with the connecting tissue being remote to the transformed position and the original horn bud position but abutting the transformed position. The horn buds can be shifted while not being completely severed from the skin so the capillaries are not severed to assure a continuous blood supply to the horn buds and skin.

The invention claimed:

1. The method of forming a one-horned animal from an animal normally having a horn bud growing from a normal position on each side of the head, comprising the steps of:
    pedicling a first flap of skin on each side of the head with each flap including the adjacent horn bud at a time prior to attachment of the bud to the skull;
    pedicling a second skin flap on each side of the front of the head in alignment with the general area of the pineal gland;
    lifting the first flaps of skin away from the skull about the attached end;
    moving the second flaps of skin into the position vacated by the adjacent first flaps of skin; and moving the first flaps of skin into the position vacated by the second flaps with the horn buds being at a transposed position adjacent one another over the pineal gland.

2. The method as defined in claim 1 wherein the first pedicled skin flaps each include a connecting tissue connecting the flap to the remaining head skin, said connecting tissue being positioned remote to the horn bud normal and transposed positions.

3. The method as defined in claim 1 wherein the second pedicled skin flaps each include a connecting tissue being positioned remote to the horn bud normal and transposed positions.

4. The method as defined in claim 3 wherein the second pedicled flaps are formed by severing the skin through the horn bud transposed position.

5. The method as defined in claim 4 wherein the horn bud of each pedicled first flap abuts the edge of the first flap.

* * * * *